United States Patent
Chen

(10) Patent No.: US 6,950,695 B2
(45) Date of Patent: Sep. 27, 2005

(54) WATCH-TYPED HEARTBEAT SENSING DEVICE

(76) Inventor: Yu-Yu Chen, 2 Fl., No. 349, Wushing St., Shinyi Chiu, Taipei (TW), 110

( * ) Notice: Subject to any disclaimer, the term of this patent is extended or adjusted under 35 U.S.C. 154(b) by 0 days.

(21) Appl. No.: 10/629,700

(22) Filed: Jul. 30, 2003

(65) Prior Publication Data

US 2005/0027200 A1 Feb. 3, 2005

(51) Int. Cl.$^7$ .............................................. A61B 5/0402
(52) U.S. Cl. .................................................... 600/509
(58) Field of Search ................................ 600/300, 502, 600/503, 509, 519, 520, 547; 968/886; 368/278, 281, 282, 283; 340/539.12; 128/903

(56) References Cited

U.S. PATENT DOCUMENTS

| | | | | |
|---|---|---|---|---|
| 3,826,246 A | * | 7/1974 | Raddi et al. ................. | 600/382 |
| 4,120,294 A | * | 10/1978 | Wolfe ........................... | 600/519 |
| 4,295,472 A | * | 10/1981 | Adams ........................ | 600/503 |
| 4,312,358 A | * | 1/1982 | Barney ........................ | 600/483 |
| 4,407,295 A | * | 10/1983 | Steuer et al. ............... | 600/483 |
| 5,226,425 A | * | 7/1993 | Righter ........................ | 600/523 |
| 5,474,077 A | * | 12/1995 | Suga ........................... | 600/500 |
| 5,778,880 A | * | 7/1998 | Chen ........................... | 600/509 |
| 6,447,456 B1 | * | 9/2002 | Tsubata ....................... | 600/455 |
| 6,537,225 B1 | * | 3/2003 | Mills ........................... | 600/481 |
| 6,547,728 B1 | * | 4/2003 | Cornuejols .................. | 600/300 |
| 6,675,041 B2 | * | 1/2004 | Dickinson ................... | 600/509 |
| 6,754,517 B2 | * | 6/2004 | Nissilä ........................ | 600/384 |

* cited by examiner

*Primary Examiner*—Jeffrey R. Jastrzab
(74) *Attorney, Agent, or Firm*—Rosenberg, Klein & Lee

(57) ABSTRACT

A watch-typed heartbeat sensing device includes a casing which defines a hollow space for the mounting of a circuit board provided with a plurality of contacts and a control circuit. The casing has two ends, a first end being mounted with a first pair of conductors which includes an inner plate and an outer plate, the two plates respectively connecting to a first and second contacts of the circuit board, a second end being mounted with a second pair of conductors which comprises an inner plate and an outer plate, the two plates respectively connecting to a third and fourth contacts of the circuit board. When a user puts on the heartbeat sensing device, the inner plates contacts wrist of the user, and when he puts his other hand on the heartbeat sensing device and touches the outer plates, two pairs of heartbeat signals are generated and transmitted to the circuit board, so that the heartbeat of the user is calculated and displayed.

5 Claims, 5 Drawing Sheets

WATCH-TYPED HEARTBEAT SENSING DEVICE

BACKGROUND OF THE INVENTION

1. Field of the Invention

The present invention relates to a heartbeat sensing device, especially to a watch-typed heartbeat sensing device.

2. Description of the Prior Art

Heartbeat sensing device is a device for detecting and displaying a heartbeat of a user. It has been widely applied in various devices for medical diagnosis and sporting purposes. By means of the heartbeat sensing device, a heartbeat is detected and displayed, thereby a user or doctor can monitor the body status of the user or patient. For example, a heartbeat sensing device is commonly installed to work in coordination with an exercise equipment. The heartbeat of the exerciser is detected and shown via a display unit of the heartbeat sensing device. Moreover, the heartbeat sensing device may be equipped with other devices like audio device, alarm and so on, so as to provide the user multiple practical functions.

Basically, a heartbeat sensing device comprises a rubber conductor which is an electrode capable of detecting a heartbeat signal and a control circuit for processing the heartbeat signal. The rubber conductor is electrically connected to the control circuit, and the heartbeat signal detected by the rubber conductor is transmitted to the processing circuit of the control circuit for processing and then displayed in a display unit.

For a wireless heartbeat sensing device, besides the rubber conductor and control circuit, it further comprises a wireless transmitting circuit which emits the heartbeat signal wirelessly to a remote receiver which is positioned within an effective distance from the heartbeat sensing device. The remote receiver receives and displays the signal.

Currently, various types of heartbeat sensing device are available in the market. Some the heartbeat sensing devices are in the form of a watch. The watch-typed heartbeat sensing device is fitted on the wrist of the user for detecting the heartbeat.

In the operation of heartbeat sensing device, the electrical connection between the rubber connector and the control circuit is a critical part that affects the effective and precise transmission of the heartbeat signal. In the past few years, the manufacturers have been aimed and devoted to develop a good electrical connection that precisely transmits the heartbeat signal with high fidelity.

In the conventional design of electrical connection, the heartbeat sensing device generally comprises a conductive plate which is mounted at the bottom of the heartbeat sensing device. Thereby, the conductive plate directly contacts the user's body and detects his heartbeat.

FIG. 1 shows a conventional watch-typed heartbeat sensing device. As shown, the heartbeat sensing device 100a comprises a display device 10a and a first conductive contact 10b at the top surface. There is a second conductive contact at the bottom of the heartbeat sensing device 110a. When the watch-typed heartbeat sensing device 100a is put on the wrist of a user, the second conductive contact directly contacts the user's wrist. When the user touches the first conductive contact 10b with the other hand, the control circuit inside the heartbeat sensing device 100a detects the heartbeat of the user and transmits a signal to the display device 10a for displaying. However, such a watch-typed heartbeat sensing device has many drawbacks, including poor electrical connection, weak heartbeat signal, low fidelity and low precision caused by poor contact between the second conductive contact and the user's wrist, surface staining, wetting, abrasion and vibration. Those problems frequently happen in watch-typed heartbeat sensing device, and affect the normal operation and shorten the service life of heartbeat sensing device.

SUMMARY OF THE INVENTION

Consequently, a primary object of the present invention is to provide a watch-typed heartbeat sensing device which has an improved excellent electrical connection. It eliminates the problems of low fidelity and weak signal.

Another problem of the present invention is to provide a watch-typed heartbeat sensing device which comprises four conductive contacts. With the four conductive contacts, the heartbeat of user can be precisely detected.

To achieve the above objects, in accordance with the present invention, there is provided a watch-typed heartbeat sensing device including a casing which defines a hollow space for the mounting of a circuit board provided with a plurality of contacts and a control circuit. The casing has two ends, a first end being mounted with a first pair of conductors which includes an inner plate and an outer plate, the two plates respectively connecting to a first and second contacts of the circuit board; a second end being mounted with a second pair of conductors which comprises an inner plate and an outer plate, the two plates respectively connecting to the third and fourth contacts of the circuit board. When a user puts on the heartbeat sensing device, the inner plates contacts the wrist of the user, and when he puts the other hand on the heartbeat sensing device and touches the outer plates, two pairs of heartbeat signals are generated and transmitted to the circuit board, so that the heartbeat of the user is calculated by a microprocessor and displayed in a display unit.

BRIEF DESCRIPTION OF THE DRAWINGS

The present invention will be apparent to those skilled in the art by reading the following description of preferred embodiments thereof, with reference to the attached drawings, in which.

DETAILED DESCRIPTION OF THE PREFERRED EMBODIMENTS

Figure 1:
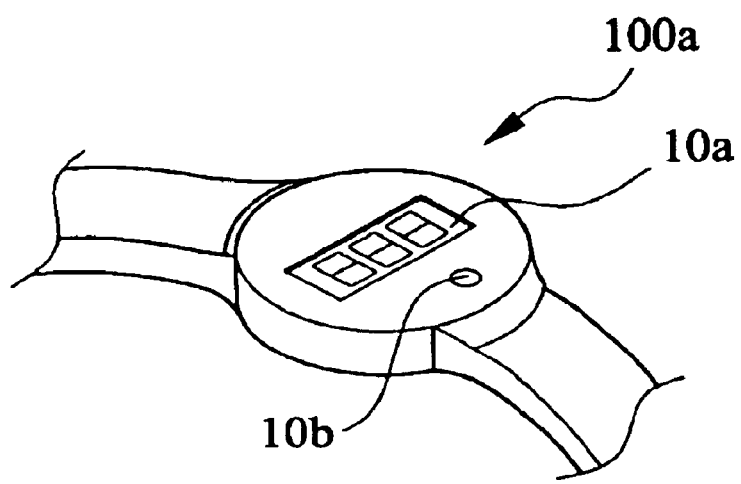
FIG. 1 is a perspective view of a conventional watch-typed heartbeat sensing device.
Figure 2:
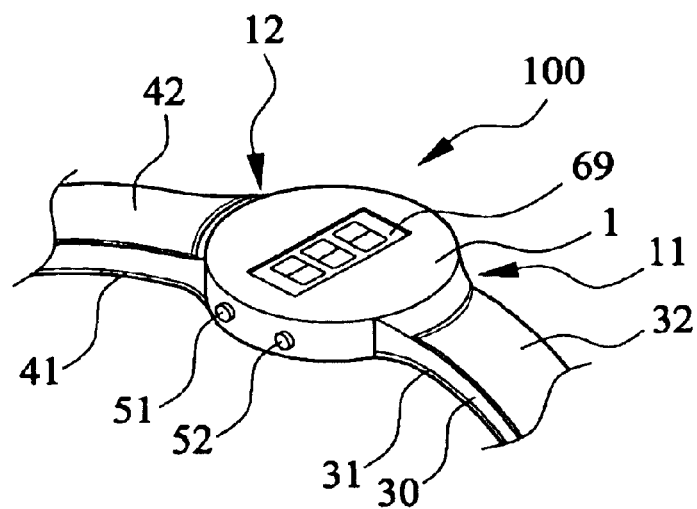
FIG. 2 is a perspective view of a watch-typed heartbeat sensing device constructed in accordance with a preferred embodiment of the present invention.
Figure 3:
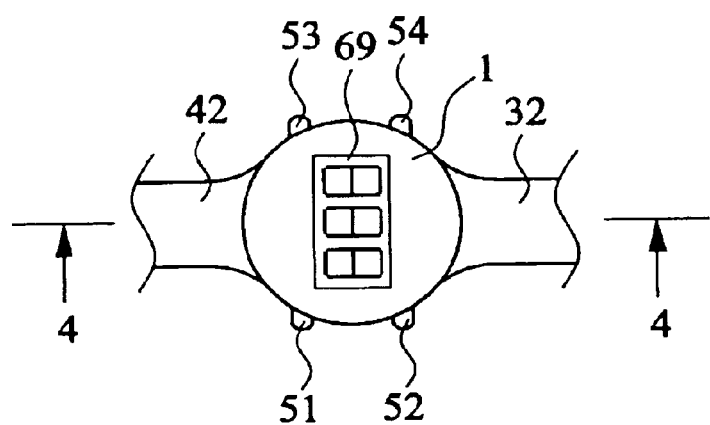
FIG. 3 is a top view of the watch-typed heartbeat sensing device of FIG. 2.

With reference to the drawings and in particular to FIG. 2, a watch-typed heartbeat sensing device constructed in accordance with a preferred embodiment of the present invention is shown. FIG. 3 is a top view of the watch-typed heartbeat sensing device of FIG. 2. As shown, the watch-typed heartbeat sensing device 100 comprises a casing 1 which is configured in the form of a watch having a first end 11 and a second end 12 in corresponding to the first end 11. The first and second ends 11, 12 of the casing 1 are connected with a watch band 30 for holding to a user's wrist. The casing 1 defines an internal hollow space for receiving a circuit board 2 and other electrical components like integrated circuit, battery and so on. The circuit board 2 comprises a control circuit for controlling the operation of the heartbeat sensing device. The circuit board 2 also comprises four contacts, namely a first contact 21, a second contact 22, a third contact 23 and a fourth contact 24. The four contacts are electrically conductive.

Figure 4:
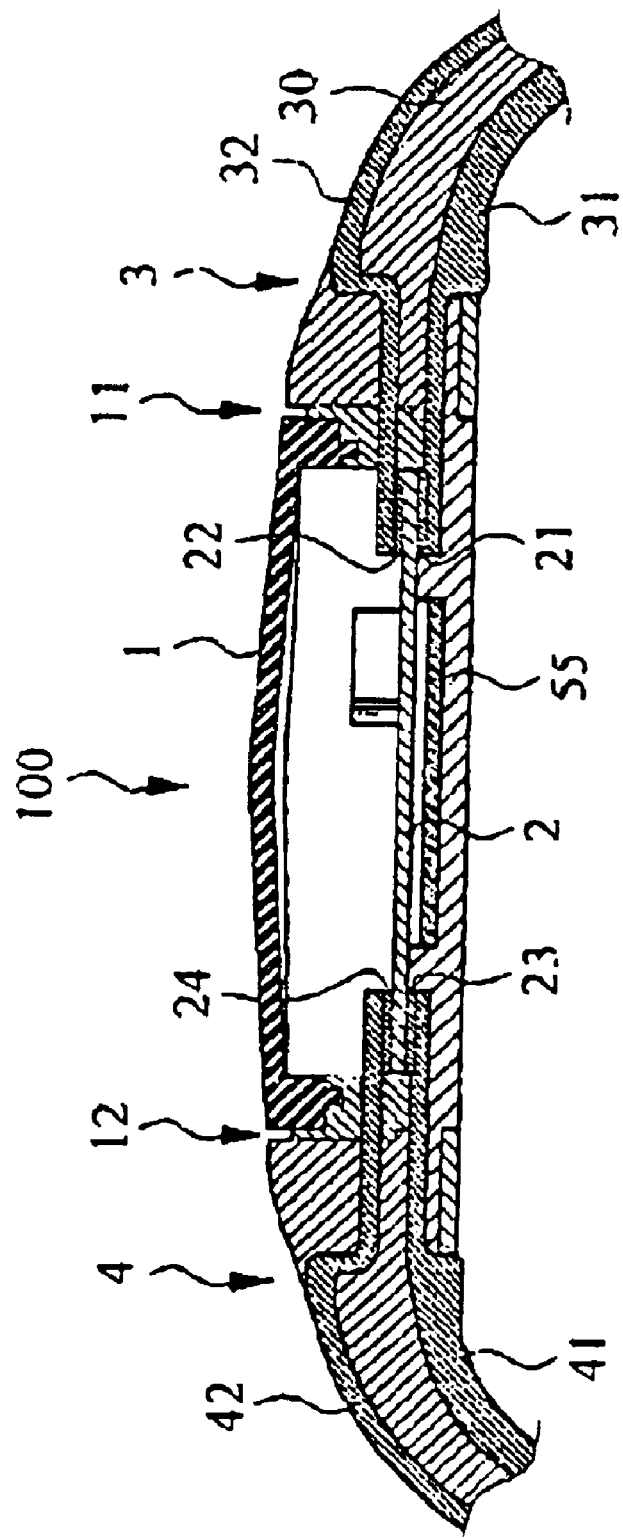
FIG. 4 is a sectional view of the watch-typed heartbeat sensing device along line 4—4 of FIG. 3.

Please also refer to FIG. 4. FIG. 4 shows a sectional view of the heartbeat sensing device along line 4—4 of FIG. 3. A first pair of conductors 3 is mounted at the first end 11. The first pair of conductors 3 comprises an inner plate 31 and an outer plate 32. One end of the inner plate 31 and the outer plate 32 are respectively connected the first contact 21 and second contact 22.

The electrical connection between the inner plate 31 and outer plate 32 and the first contact 21 and second contact 22 of the circuit board 2 is accomplished by electric welding. Other connection measures by e.g. plugging of pins, press contact and so on may also be applied.

Similarly, a second pair of conductors 4 is mounted at the second end 12 in correspondence to the first pair of conductors 3, which comprises an inner plate 41 and an outer plate 42. The inner plate 41 and outer plate 42 are respectively connected to the third contact 23 and the fourth contact 24.

Figure 5:
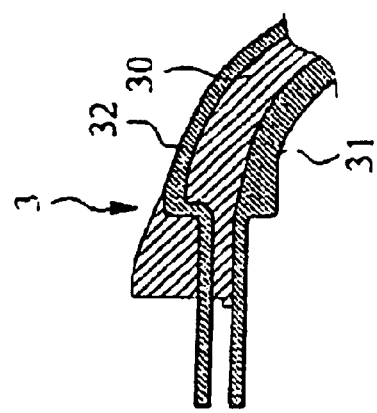
FIG. 5 is a sectional view showing an integral structure of a watch band with an inner plate and an outer plate of the present invention.

In embodying the present invention, the inner plates 31, 41 and corresponding outer plates 32, 42 of the first and second pair of conductors 3, 4 can be formed integrally with the watch band. FIG. 5 shows a sectional view of the watch band of the heartbeat sensing device, in which the inner plate 31 and the outer plate 32 are respectively formed on a bottom surface and an upper surface of the watch band and adjacent to the first end of the casing. The integrated watch band is directly plugged to the first end 11 of heartbeat sensing device 100 and connected with the first and second contacts 21, 22.

When the watch-typed heartbeat sensing device 100 is put on a wrist of a user by means of the watch band, the inner plate 31 of the first pair of conductors 3 and the inner plate 41 of the second pair of conductors 4 contact directly with the user's wrist, while the outer plate 32 of the first pair of conductors 3 and the outer plate 42 of the second pair of conductors 4 allow the contact of the other hand of the user. In other words, the watch-typed heartbeat sensing device 100 provides four external contacts at the watch band 30, the inner plates 31, 41, and the outer plates 32, 42. Accordingly, when the user touches the watch-typed heartbeat sensing device 100 with his hands, two signals are generated respectively and sent to the first pair of conductors 3 and the second pair of conductors 4. Thereby, the control circuit of heartbeat sensing device 100 detects the heartbeat of user.

Preferably, the casing 1 is mounted with a plurality of control buttons for setting and control of the various functions of the heartbeat sensing device 100. For example, a set button 51 is provided for setting the various parameters e.g. alarm for high heartbeat rate, time and so on of the heartbeat sensing device 100.

Furthermore, the casing 1 is mounted with a switch button 52 for switching the function modes of the heartbeat sensing device 100. The function modes include time display mode, heartbeat sensing mode and so on. A start/stop button 52 is also mounted on the casing 1 for starting up or stopping the detection of heartbeat.

Also, a backlight button 54 is mounted on the casing 1 for turning on a backlight 55 of the heartbeat sensing device 100. The backlight 55 is disposed in the hollow space of the casing 1 for providing lighting.

Figure 6:
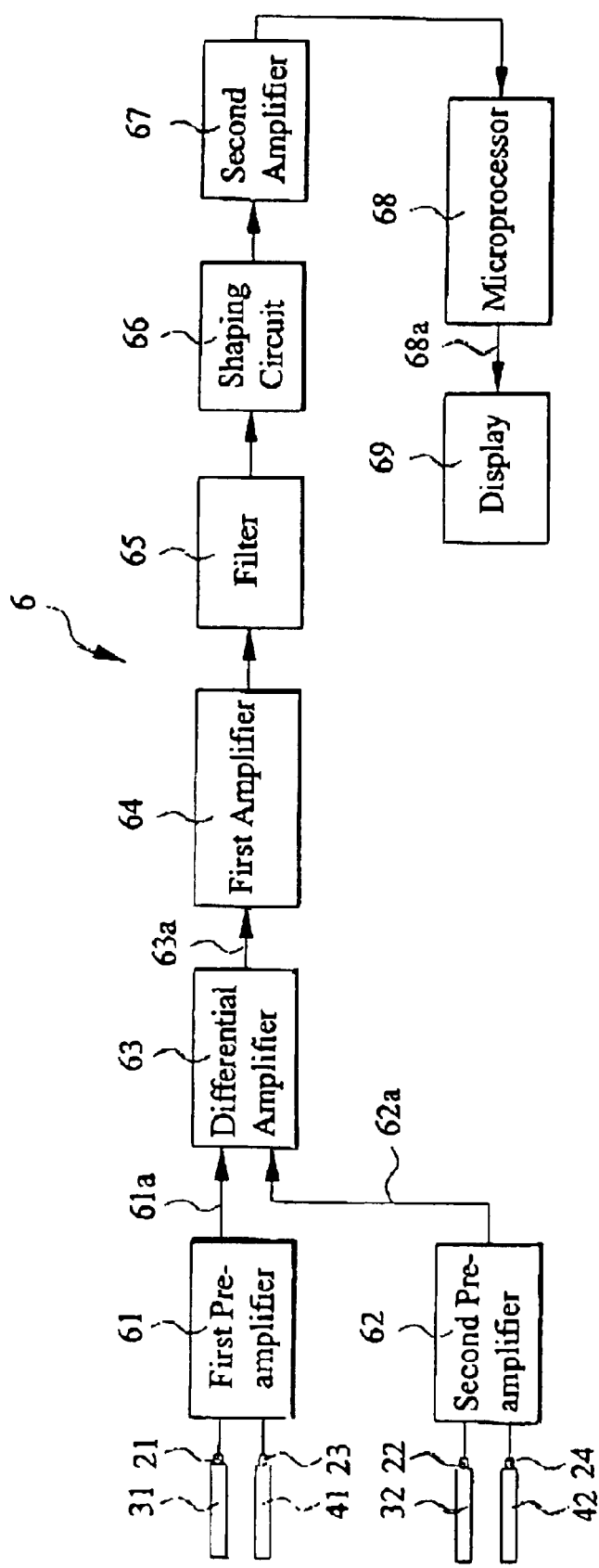
FIG. 6 is a block diagram of the control circuit of the present invention.

FIG. 6 shows the circuit block diagram of the control circuit of the present invention. The control circuit 6 comprises a first pre-amplifier 61, a second pre-amplifier 62, a differential amplifier 63, a first amplifier 64, a filter 65, a shaping circuit 66, a second amplifier 67, a microprocessor 68 and a display 69.

The first pre-amplifier 61 comprises two input terminals, a first input terminal being connected to the first contact 21 and through which to the inner plate 31 of the first pair of conductors 3, the second input terminal being connected to the third contact 23 and through which to the inner plate 41 of the second pair of conductors 4. When the watch-typed heartbeat sensing device 100 is put on the wrist of the user, a first differential signal 61a is generated.

The second pre-amplifier 62 comprises two input terminals, a first input terminal being connected to the second contact 22 and through which to the plate 32 of the first pair of conductors 3; a second input terminal being connected to the fourth contact 24 and through which to the outer plate 42 of the second pair of conductors 4. When the watch-typed heartbeat sensing device 100 is touched by other hand of the user, a first differential signal 62a is generated.

The differential amplifier 63 comprises two input terminals. A first input terminal is connected to the first pre-amplifier 61 for receiving the first differential signal 61a, while a second input terminal is connected to the second pre-amplifier 62 for receiving a second differential signal 62a. The differential amplifier 63 generates a differential output signal 63a based on the difference between the first differential signal 61a and the second differential signal 62a.

The differential output signal 63a is transmitted to the first amplifier 64 for amplifying. The differential output signal 63a is filtered by the filter 66 to reduce the noise. The filtered signal is then shaped by the shaping circuit 66, and further amplified by a second amplifier 67.

The amplified signal is then forwarded from the second amplifier 67 to the microprocessor 68 for processing and calculation. The microprocessor 68 generates a heartbeat signal 68a to the display 69 for displaying.

With the embodiments described above, it is understood that the present invention provides an improved watch-typed heartbeat sensing device that can precisely detect the user's heartbeat and eliminates the problem of low fidelity or weak heartbeat signal. As a whole, it is practical for use and superior to similar product available in the market.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A watch-typed heartbeat sensing device for detecting at least one heartbeat signal of a user, comprising:
    a casing having an internal hollow space a first end, and a second end;

a watch band with two ends respectively connected to the first end and the second end of the casing;

a circuit board mounted in the hollow space of the casing, the circuit including a first contact, a second contact, a third contact, a fourth contact and a control circuit, the control circuit including:

a first pre-amplifier having a first input terminal connected to the first contact of the circuit board and a second input terminal connected to the third contact of the circuit board for generating a first differential signal at an output terminal thereof;

a second pre-amplifier having a first input terminal connected to the second contact of the circuit board and a second input terminal connected to the fourth contact of the circuit board for generating a second differential signal at an output terminal thereof;

a differential amplifier having first and second differential signal input terminals, the first differential signal input terminal being connected to the output terminal of the first pre-amplifier for receiving the first differential signal, the second differential signal input terminal being connected to the output terminal of the second pre-amplifier for receiving the second differential signal, the differential amplifier generating a differential output signal at an output terminal thereof based on the difference between the first differential signal and the second differential signal;

a microprocessor coupled the output terminal of the differential amplifier for receiving the differential output signal, the microprocessor calculating and then outputting a heartbeat signal; and a display coupled to the microprocessor for receiving the heartbeat signal therefrom and displaying the heartbeat signal;

a first pair of conductors mounted at the first end of the casing, the first pair of conductors including an inner plate and an outer plate respectively electrically connected to the first contact and the second contact of the circuit board; and a second pair of conductors mounted at the second end of the casing, the second pair of conductors including an inner plate and an outer plate and respectively electrically connected to the third contact and the fourth contact of the circuit board;

wherein when the casing is put on a wrist of one hand of the user by means of the watch band, the inner plate of the first pair of conductors and the inner plate of the second pair of conductors contact the wrist of the user, and when the user puts his other hand onto the casing of the heartbeat sensing device and contacts the outer plate of the first pair of conductors and the outer plate of the second pair of conductors, thereby two pairs of heartbeat signals are generated respectively at the first pair of conductors and the second pair of conductors and transmitted to the control circuit of the circuit board.

2. The watch-typed heartbeat sensing device as claimed in claim 1, wherein the control circuit further comprises a filter which is connected between the differential amplifier and the microprocessor for filtering the noise of the differential output signal received from the differential amplifier.

3. The watch-typed heartbeat sensing device as claimed in claim 2, wherein the control circuit further comprises a shaping circuit which is connected between the filter and the microprocessor for shaping the heartbeat signal received from the filter.

4. The watch-typed heartbeat sensing device as claimed in claim 1, wherein the inner plate and the outer plate of the first pair of conductors is integrally formed on a bottom surface and an upper surface of the watch band and adjacent to the first end of the casing.

5. The watch-typed heartbeat sensing device as claimed in claim 1, wherein the inner plate and the outer plate of the second pair of conductors is integrally farmed on a bottom surface and an upper surface of the watch band and adjacent to the second end of the casing.

\* \* \* \* \*